United States Patent
Kim et al.

(12) 
(10) Patent No.: US 12,011,321 B2
(45) Date of Patent: Jun. 18, 2024

(54) AUTOMATED APPARATUS FOR STEREOTACTIC SURGICAL DEVICE

(71) Applicant: SEOUL NATIONAL UNIVERSITY R&DB FOUNDATION, Seoul (KR)

(72) Inventors: Sung Yon Kim, Seoul (KR); Hyun Ju Ahn, Hanam-si (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 285 days.

(21) Appl. No.: 17/694,177

(22) Filed: Mar. 14, 2022

(65) Prior Publication Data

US 2022/0287791 A1    Sep. 15, 2022

(30) Foreign Application Priority Data

Mar. 15, 2021    (KR) .......................... 10-2021-0033259

(51) Int. Cl.
    *A61B 90/10*    (2016.01)
(52) U.S. Cl.
    CPC .................. *A61B 90/10* (2016.02)
(58) Field of Classification Search
    CPC ......... A61B 90/10; A61B 34/00; A61B 34/20; A61B 34/30; A61B 34/32; A61B 34/70; A61B 34/74; A61B 2034/304; A61B 2034/305
    See application file for complete search history.

(56) References Cited

U.S. PATENT DOCUMENTS

| | | |
|---|---|---|
| 6,258,103 B1 | 7/2001 | Saracione |
| 2005/0107680 A1 | 5/2005 | Kopf et al. |
| 2013/0172903 A1* | 7/2013 | Suarez ................... A61B 34/30 606/1 |
| 2018/0116759 A1* | 5/2018 | Chen ...................... A61B 90/50 |

FOREIGN PATENT DOCUMENTS

WO    WO-2019132279 A1 *    7/2019    ......... A61B 17/1693

* cited by examiner

*Primary Examiner* — Robert A Lynch
(74) *Attorney, Agent, or Firm* — CANTOR COLBURN LLP

(57) ABSTRACT

Provided is an automated apparatus for a stereotactic surgical device capable of applying a rotational force to a handle of the stereotactic surgical device. The apparatus includes a support that is formed into a plate shape including therein a first opening and is coupled to the stereotactic surgical device, an operation part that is coupled to the handle penetrating the support and has a receiving groove, which is extended in a longitudinal direction, at an upper portion, a driving part that includes a rotational shaft, a rotational part that includes an insertion member to be inserted into the receiving groove and is coupled to the rotational shaft, and a connection part which is coupled to the driving part by receiving the rotational part in a chamber formed therein and of which the lower portion is detachably coupled to the support.

12 Claims, 10 Drawing Sheets

AUTOMATED APPARATUS FOR STEREOTACTIC SURGICAL DEVICE

TECHNICAL FIELD

The present invention relates to an automated apparatus for stereotactic surgical device, and more particularly to an automated apparatus for stereotactic surgical device that is detachably coupled to a stereotactic surgical device and can automatically move a surgical instrument of the stereotactic surgical device.

BACKGROUND

Stereotactic surgery is a surgery for inserting an optical fiber or an electrode or injecting a drug or a viral vector into a specific area of the brain. The specific area of the brain undergoing stereotactic surgery is micrometer sized and thus needs surgery with high accuracy and precision.

In general, a stereotactic surgical device for stereotactic surgery may be a device (hereinafter, referred to as "stereotactic surgical device") that can be manually operated by a user or a device (hereinafter, referred to as "automated stereotactic surgical device") that can be automatically operated by using electric energy.

The stereotactic surgical device is equipped with a plurality of handles for moving a surgical instrument on an x-axis, a y-axis and a z-axis, respectively, and can move the surgical instrument when the user turns the handles. The automated stereotactic surgical device drives a motor or the like with electric energy and can move the surgical instrument on the x-axis, the y-axis and the z-axis by using a driving power of the motor.

Meanwhile, in order to minimize damage to the brain tissue, the surgical instrument needs to be inserted precisely into the specific area of the brain at a very slow rate. Therefore, the user of the stereotactic surgical device has to manipulate the handles slowly for a long time.

Although the user of the automated stereotactic surgical device does not have to manipulate a handle, the stereotactic surgical device costs a lot to prepare.

Accordingly, there is a need to develop an apparatus capable of automating a stereotactic surgical device which can be manually operated at a reasonable cost.

SUMMARY

The present invention is conceived to provide an automated apparatus for stereotactic surgical device that is attached to a stereotactic surgical device and can automate the stereotactic surgical device.

Further, the present invention provides an automated apparatus for stereotactic surgical device that can switch a stereotactic surgical device into a manual mode or an automatic mode.

Furthermore, the present invention provides an automated apparatus for stereotactic surgical device that can control a stereotactic surgical device according to a user's instruction.

However, the problems to be solved by the present invention are not limited to the above-described problems. Although not described herein, other problems to be solved by the present invention can be clearly understood by a person with ordinary skill in the art from the following descriptions.

An aspect of the present invention provides an automated apparatus for stereotactic surgical device. The automated apparatus for stereotactic surgical device capable of applying a rotational force to a handle of a stereotactic surgical device includes a support that is formed into a plate shape including therein a first opening and is coupled to the stereotactic surgical device in order for the handle to the first opening, an operation part that is coupled to the handle penetrating the support and has a receiving groove, which is extended in a longitudinal direction, at an upper portion, a driving part that includes a rotational shaft, a rotational part that includes an insertion member extended in the longitudinal direction to be inserted into the receiving groove and is coupled to the rotational shaft, and a connection part which is coupled to the driving part by receiving the rotational part in a chamber formed therein and includes a second opening at a lower portion to communicate with the chamber and allow the operation part to be introduced thereinto and of which the lower portion is detachably coupled to the support. When the connection part is attached to the support, the operation part may be introduced into the second opening and the insertion member of the rotational part is inserted into the operation part, and when the connection part is detached from the support, the insertion member of the rotational part may be separated from the operation part.

The operation part may include a first operation member that includes a first receiving groove at an upper portion and a first contact surface, which is capable of being in contact with the handle, at a first lateral portion, a second operation member that includes a second receiving groove at an upper portion and a second contact surface, which faces the first contact surface and is capable of being in contact with the handle, at a second lateral portion, and a coupling member that couples the first operation member and the second operation member and is capable of adjusting a distance between the first operation member and the second operation member.

Also, the support may include at least one support bolt, at least one support nut capable of being screw-coupled to the at least one support bolt, a plurality of bolt insertion holes, which is formed to allow the at least one support bolt to be inserted thereinto and faces each other, at a lateral portion of the support, and a nut insertion hole that is formed to communicate with the bolt insertion hole and penetrates an upper portion and a lower portion of the support to allow the support nut to be inserted thereinto. When the support bolt inserted into the bolt insertion hole, which is screw-coupled to the support nut inserted into the nut insertion hole, is tightened, the support coupled to the stereotactic surgical device may be fixed to the stereotactic surgical device.

Further, the support may include a plurality of protrusions at the upper portion and the connection part includes a plurality of grooves at the lower portion. The protrusions may be freely inserted into the groove or freely separated from the groove. When the protrusions are inserted into the groove, lateral rotation and lateral movement between the connection part and the support may be limited.

Furthermore, the coupling member may include operation part bolts screw-coupled to the first operation member and the second operation member, respectively, and an operation part nut capable of fixedly coupling to a screw column.

Moreover, the rotational shaft is configured to be rotated by a step motor.

The automated apparatus for stereotactic surgical device may also include a controller capable of controlling any one or more of a rotational direction, a rotational speed and an operation time of the rotational shaft.

The controller may include an input member that receives a user's operational instruction and a display member that displays any one or more of a time required for operating the rotational shaft, a remaining operation time of the rotational shaft, a moving speed of a surgical instrument of the stereotactic surgical device and a moving range of the surgical instrument. The rotational speed and the operation time of the rotational shaft may be calculated based on the required moving range and moving speed of the surgical instrument input by the user.

Details of other exemplary embodiments will be included in the detailed description and the accompanying drawings.

According to an embodiment of the present invention, in the automated apparatus for stereotactic surgical device, the connection part coupled to the driving part is attached to the support coupled to the stereotactic surgical device so that the rotational part is coupled to the operation part coupled to the handle and rotates the operation part. Thus, the automated apparatus for stereotactic surgical device can automate the stereotactic surgical device.

According to an embodiment of the present invention, when the connection part coupled to the driving part is attached to the support, the rotational part is coupled to the operation part to switch the stereotactic surgical device into an automated stereotactic surgical device. When the connection part coupled to the driving part is detached from the support, the rotational part is separated from the operation part to switch the automated stereotactic surgical device into the stereotactic surgical device.

According to an embodiment of the present invention, the automated apparatus for stereotactic surgical device includes the controller capable of controlling an operation of the driving part when the user inputs an instruction. Thus, the stereotactic surgical device can be controlled according to the user's instruction.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Figure 1:
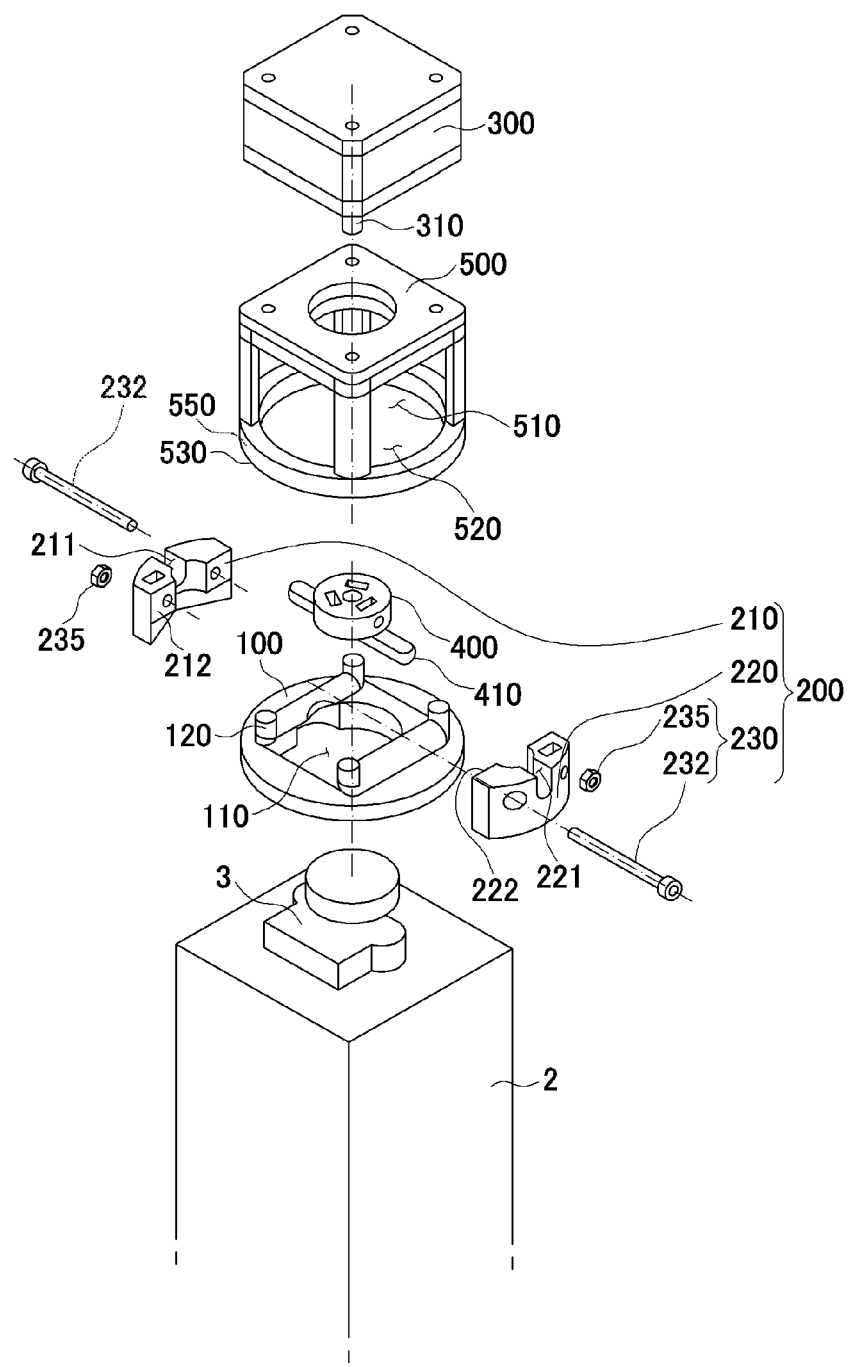
FIG. 1 is an exploded perspective view illustrating an automated apparatus for stereotactic surgical device according to an embodiment of the present invention.

Hereafter, example embodiments will be described in detail with reference to the accompanying drawings so that the present invention may be readily implemented by a person with ordinary skill in the art. However, it is to be noted that the present invention is not limited to the example embodiments but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected to" another element and an element being "electronically connected to" another element via another element.

Through the whole document, the term "on" that is used to designate a position of one element with respect to another element includes both a case that the one element is adjacent to the other element and a case that any other element exists between these two elements.

Further, it is to be understood that the term "comprises or includes" and/or "comprising or including" used in the document means that one or more other components, steps, operation and/or the existence or addition of elements are not excluded from the described components, steps, operation and/or elements unless context dictates otherwise; and is not intended to preclude the possibility that one or more other features, numbers, steps, operations, components, parts, or combinations thereof may exist or may be added. The term "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party. Through the whole document, the term "step of" does not mean "step for".

Hereafter, exemplary embodiments of the present invention will be described in detail with reference to the accompanying drawings. However, the present invention is not limited to the following exemplary embodiments and can be embodied in a different form. Like reference numerals generally denote like elements throughout the present specification.

Hereafter, a configuration of an automated apparatus for stereotactic surgical device 1 according to an embodiment of the present invention will be described.

FIG. 1 is an exploded perspective view illustrating an automated apparatus for stereotactic surgical device according to an embodiment of the present invention.

Referring to FIG. 1, the automated apparatus for stereotactic surgical device 1 includes a support 100, an operation part 200, a driving part 300, a rotational part 400 and a connection part 500.

In the present invention, a direction from the support 100 toward the driving part 300 will be referred to as an upward direction, a direction from the driving part 300 toward the support 100 will be referred to as a downward direction, and a direction orthogonal to the upward or downward direction will be referred to as a lateral direction.

Also, in the present invention, a portion of a component located in the upward direction will be referred to as an upper portion, a portion located in the downward direction will be referred to as a lower portion, and a portion located in the lateral direction will be referred to as a lateral portion.

First, the support 100 will be described.

Figure 2A:
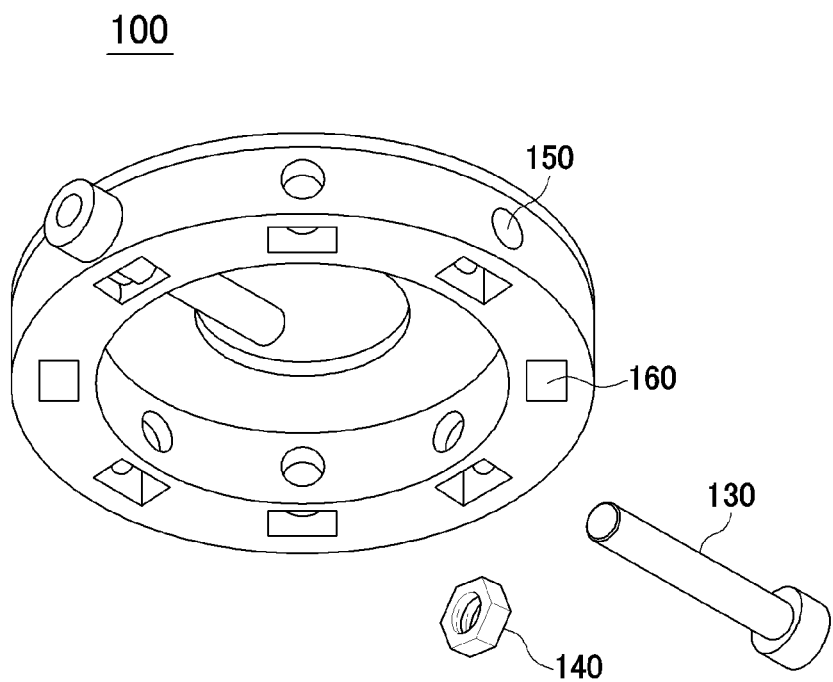
FIG. 2A is a perspective view illustrating a support of the automated apparatus for stereotactic surgical device when viewed from below according to an embodiment of the present invention.
Figure 2B:
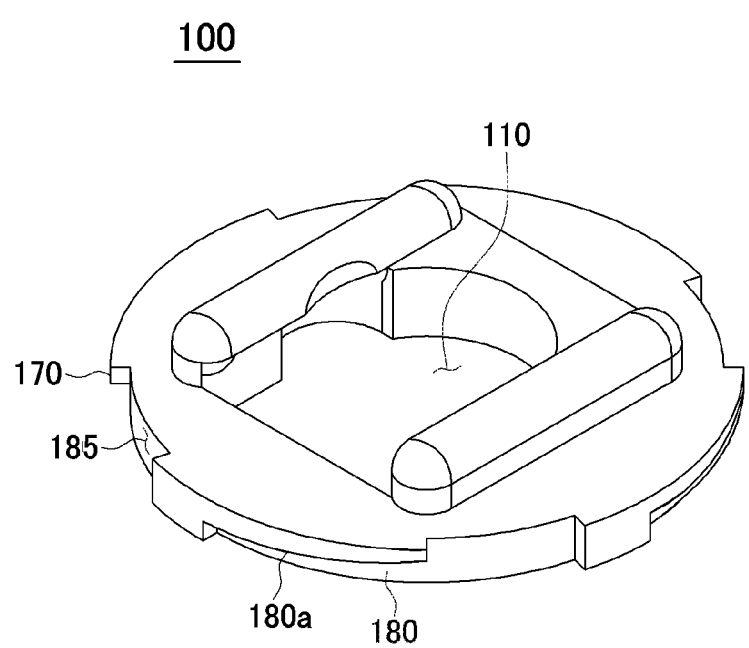
FIG. 2B is a perspective view illustrating the support according to another embodiment of the present invention.

FIG. 2A is a perspective view illustrating a support of the automated apparatus for stereotactic surgical device when viewed from below according to an embodiment of the present invention. FIG. 2B is a perspective view illustrating the support according to another embodiment of the present invention.

For example, referring to FIG. 1 and FIG. 2A, the support 100 is formed into a plate shape that allows a handle 3 of a stereotactic surgical device 2 to penetrate therethrough and can be coupled to the stereotactic surgical device 2, and includes a first opening 110, a protrusion 120, a support bolt 130, a support nut 140, a bolt insertion hole 150 and a nut insertion hole 160.

For another example, referring to FIG. 2B, the support 100 is formed into a circular plate shape including the first opening 110, and includes an outer circular portion 170 including a plurality of circular arc-shaped insertion grooves 185 and an inner circular groove 180. The support 100 including the outer circular portion 170 and the inner circular groove 180 will be described later with reference to the connection part 500 illustrated in FIG. 5.

The first opening 110 is an opening formed in the support 100 to allow the handle 3 to penetrate therethrough.

A plurality of protrusions 120 each having a predetermined shape is formed at an upper portion of the support 100. For example, the plurality of protrusions 120 may be formed at the upper portion of the support 100 along an outer periphery of the first opening 110. Also, the protrusion 120 may be inserted into a groove 530 of the connection part 500 to be described later.

The support bolt 130 may be configured as a conventional bolt having a screw thread on its outer peripheral surface and may be inserted into the bolt insertion hole 150 to be described later.

The support nut 140 may be configured as a conventional nut having a screw thread on its inner peripheral surface and may be inserted into the nut insertion hole 160 to be described later and screw-coupled to the support bolt 130.

The bolt insertion hole 150 is a hole formed at a lateral portion of the support 100 to allow the support bolt 130 to be inserted thereinto. Also, a plurality of bolt insertion holes 150 may be formed in the support 100 so as to face each other.

The nut insertion hole 160 is formed to communicate with the bolt insertion hole 150 and may penetrate the upper portion and a lower portion of the support 100 so that the support nut 140 can be inserted into the nut insertion hole 160.

Meanwhile, when the support bolt 130 inserted into the bolt insertion hole 150, which is screw-coupled to the support nut 140 inserted into the nut insertion hole 160, is tightened, a predetermined portion of the stereotactic surgical device 2 coupled to the support 100 is pressed by the bolt 130 so that the support 100 can be stably fixed to the stereotactic surgical device 2.

Figure 3:
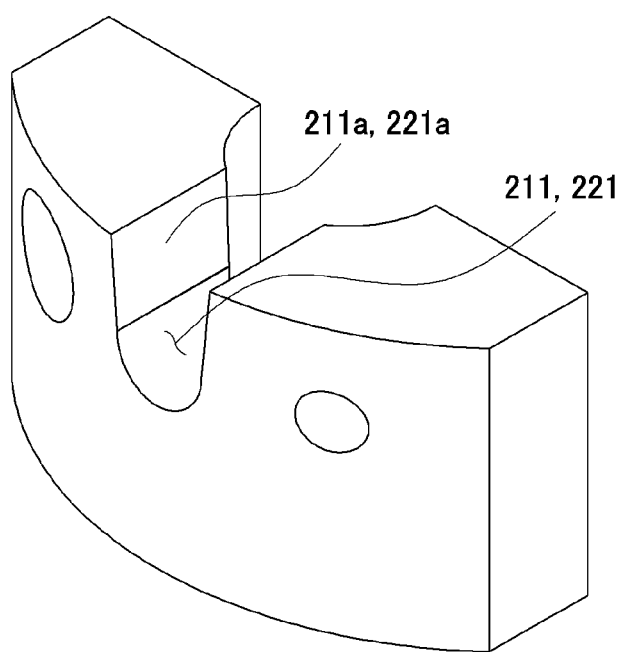
FIG. 3 is a perspective view illustrating a first operation member or a second operation member of an operation part according to an embodiment of the present invention.

FIG. 3 is a perspective view illustrating a first operation member or a second operation member of an operation part according to an embodiment of the present invention.

Hereafter, the operation part 200 will be described.

Referring to FIG. 1 and FIG. 3, the operation part 200 can be coupled to the handle 3 penetrating the support 100, and includes a first operation member 210, a second operation member 220 and a coupling member 230.

The first operation member 210 includes a first receiving groove 211 at an upper portion and a first contact surface 212, which can be in contact with the handle 3, at a later portion facing the second operation member 220. The first contact surface 212 may have a curved surface so as to be in wide contact with the handle 3 having a curved surface.

The second operation member 220 may be formed to face the first operation member 210 in the lateral direction, and includes a second receiving groove 221 at an upper portion and a second contact surface 222, which can be in contact with the handle 3, at a later portion opposite to the first operation member 210. Like the first contact surface 212, the second contact surface 222 may have a curved surface so as to be in wide contact with the handle 3 having a curved surface.

The first receiving groove 211 forms a receiving groove extended in a longitudinal direction together with the second receiving groove 221, and an insertion member 410 of the rotational part 400 to be described later may be inserted into the receiving groove.

the coupling member 230 couples the first operation member 210 and the second operation member 220 and is capable of adjusting a distance between the first operation member 210 and the second operation member 220.

For example, the coupling member 230 may include an operation part bolt 232 having a screw thread so as to be screw-coupled to the first operation member 210 and the second operation member 220 and an operation part nut 235 screw-coupled to the operation part bolt 232.

Specifically, the operation part bolt 232 may be inserted into the first operation member 210 and the second operation member 220 in a direction from the first operation member 210 toward the second operation member 220 or in a direction from the second operation member 220 toward the first operation member 210.

Further, the operation part bolt 232 penetrating the first operation member 210 and the second operation member 220 may be screw-coupled to the operation part nut 235.

Therefore, when the handle 3 is located between the coupling members 230 and the operation part bolt 232 is rotated in a clockwise direction or a counterclockwise direction, a distance between the operation part bolt 232 and the operation part nut 235 connecting the first operation member 210 and the second operation member 220 is adjusted. Thus, the coupling member 230 can be stably coupled to the handle 3 which may have various sizes.

Hereafter, the driving part 300 will be described.

Referring to FIG. 1, the driving part 300 may be configured to apply a rotational force to the operation part 200 coupled to the handle 3, and includes a rotational shaft 310.

The rotational shaft 310 may be rotated, for example, by a conventional step motor disposed inside the driving part 300.

The rotational shaft 310 is coupled to the rotational part 400 and thus rotates the rotational part 400.

Figure 4:
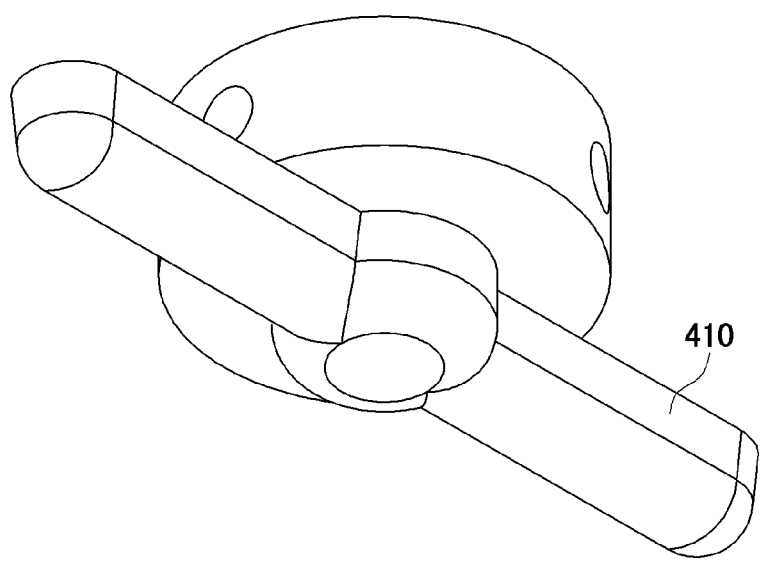
FIG. 4 is a perspective view illustrating a rotational part when viewed from below according to an embodiment of the present invention.

FIG. 4 is a perspective view illustrating a rotational part when viewed from below according to an embodiment of the present invention.

Hereafter, the rotational part 400 will be described.

Referring to FIG. 1 and FIG. 4, the rotational part 400 may be coupled to the rotational shaft 310 of the driving part 300 and may be rotated, and includes the insertion member 410 extended in a longitudinal direction so as to be inserted into the first and second receiving grooves 211 and 221 of the operation part 200.

If the rotational part 400 is rotated in a state where the insertion member 410 is inserted into the first and second receiving grooves 211 and 221, the operation part 200 coupled to the handle 3 is rotated and thus rotates the handle 3.

Specifically, referring to FIG. 3 and FIG. 4, one end of the insertion member 410 of the rotational part 400 may be inserted into the first receiving groove 211 of the first operation member 210 and the other end thereof may be inserted into the second receiving groove 221 of the second operation member 220. Herein, a transversal cross section of the insertion member 410 may have a wedge shape that tapers downwards. Also, the first receiving groove 211 and the second receiving groove 221 have a shape corresponding to the lower wedge shape of the insertion member 410, and may include a pair of slanted surfaces 211a and 221a in contact with the lower wedge shape.

Accordingly, in spite of abrasion caused by continuous friction between the insertion member 410 and the first and second receiving grooves 211 and 221 due to a rotational force generated in the rotational part 400 and the gravity, the insertion member 410 can be engaged with the first and second receiving grooves 211 and 221 without a gap.

Hereafter, the connection part 500 will be described.

Referring to FIG. 1, an upper portion of the connection part 500 may be coupled to the driving part 300 and a lower portion thereof may be detachably coupled to the support 100, and the connection part 500 includes a chamber 510, a second opening 520, the second opening 520 and the groove 530.

The chamber 510 is a space formed inside the connection part 500, and accommodated therein the rotational shaft 310 of the driving part 300 and the rotational part 400. The chamber 510 is formed to allow the rotational part 400 accommodated in the chamber 510 to be freely rotated.

The second opening 520 is formed at a lower portion of the connection part 500 so as to communicate with the chamber 510. When the connection part 500 is attached to the support 100, the operation part 200 is introduced into the chamber 510 through the second opening 520, the insertion member 410 of the rotational part 400 may be inserted into the first and second receiving grooves 211 and 221 of the operation part 200 introduced into the chamber 510.

A plurality of grooves 530 illustrated in FIG. 1 may be formed at the lower portion of the connection part 500. When the plurality of protrusions 120 of the support 100 is inserted into the plurality of grooves 530, the connection part 500 can be attached to the support 100. When the plurality of protrusions 120 of the support 100 is separated from the plurality of grooves 530, the connection part 500 can be detached from the support 100.

When the plurality of protrusions 120 of the support 100 is inserted into the plurality of grooves 530, lateral rotation and lateral movement between the connection part 500 and the support 100 are limited.

Further, when the plurality of protrusions 120 of the support 100 is separated from the plurality of grooves 530, the connection part 500 moves in an upward direction of the support 100 so as to be detached from the support 100.

Figure 5:
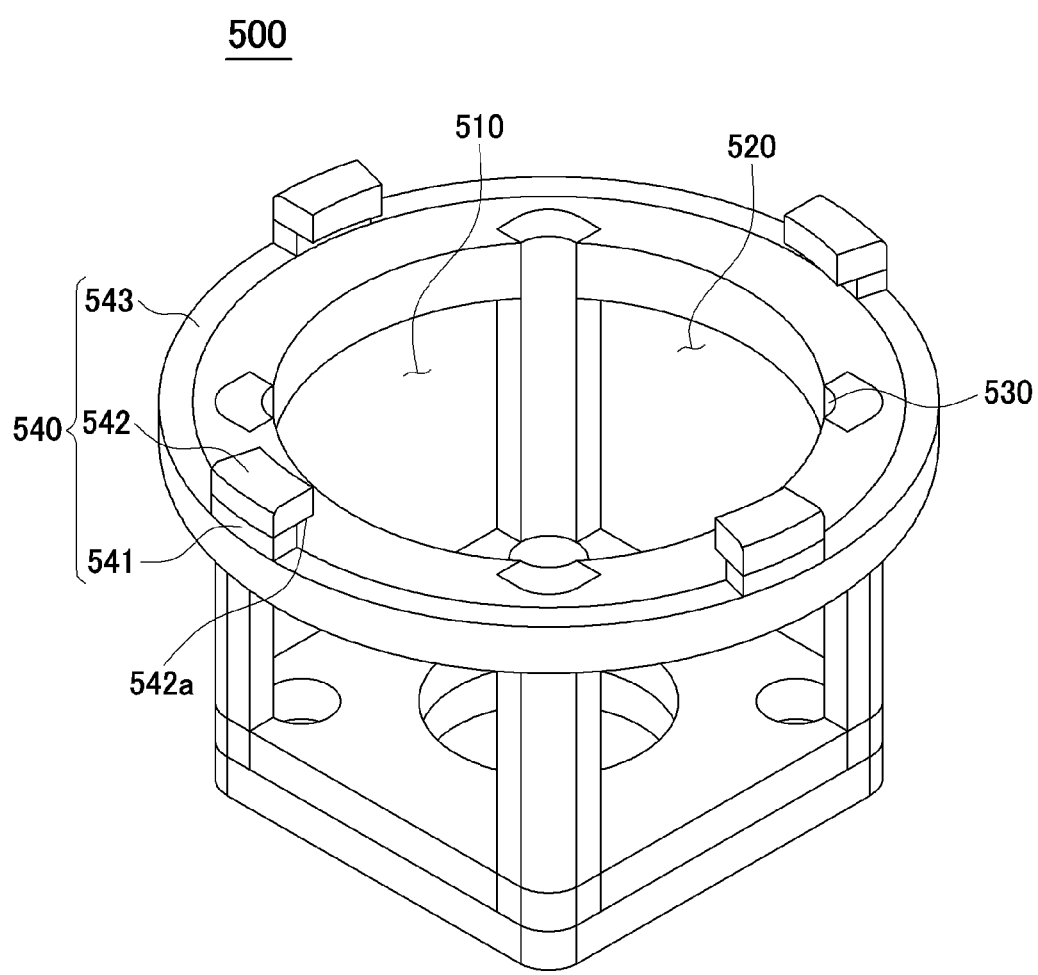
FIG. 5 is a perspective view illustrating a bottom surface of a connection part directed upwards according to an embodiment of the present invention.
Figure 6A:
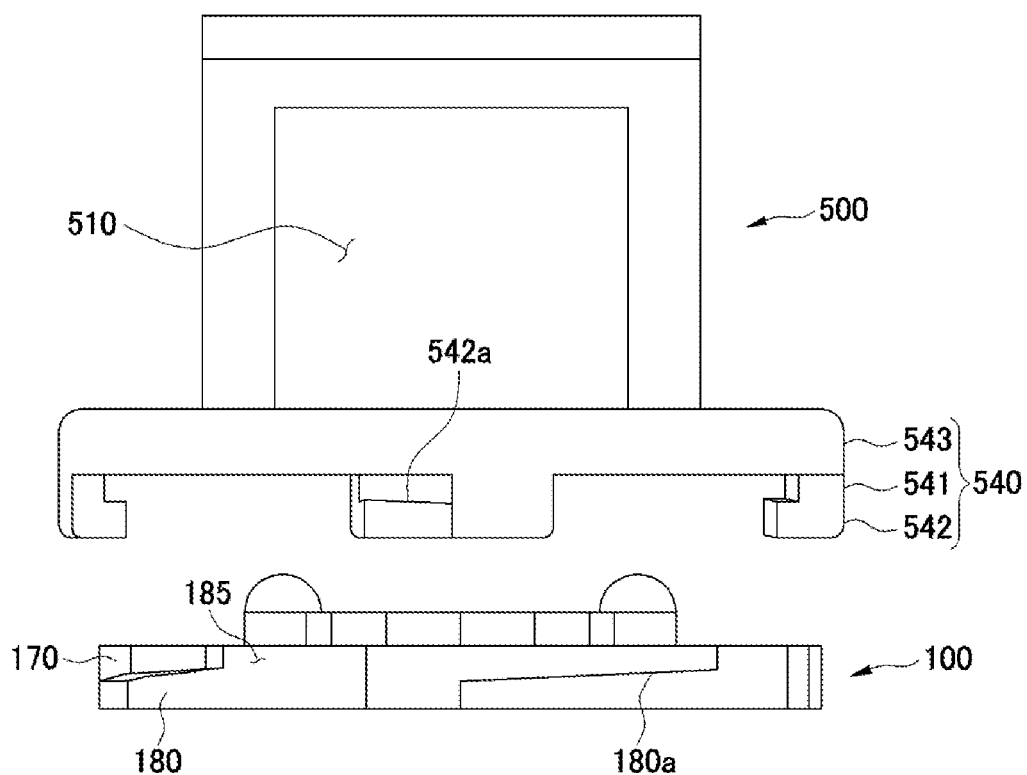
FIG. 6A is an exploded view provided to explain a coupling relationship between the support illustrated in FIG. 2B and a fastening ring illustrated in FIG. 5.
Figure 6B:
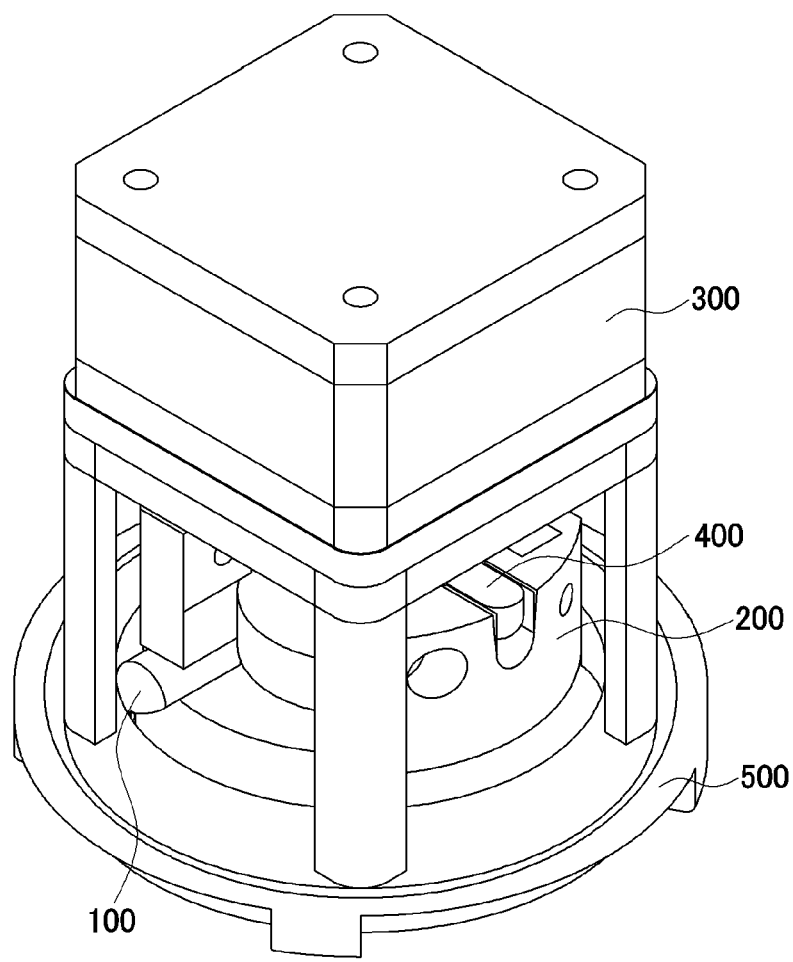
FIG. 6B is an enlarged view of the automated apparatus for stereotactic surgical device coupled to a handle of a stereotactic surgical device.

FIG. 5 is a perspective view illustrating a bottom surface of a connection part directed upwards according to an embodiment of the present invention. FIG. 6A is an exploded view provided to explain a coupling relationship between the support illustrated in FIG. 2B and a fastening ring illustrated in FIG. 5. FIG. 6B is an enlarged view of the automated apparatus for stereotactic surgical device coupled to a handle of a stereotactic surgical device.

In another embodiment, referring to FIG. 5, the connection part 500 further includes an annular fastening ring 540 disposed under the chamber 510 along the circumference of a frame 550 including the second opening 520. Herein, the fastening ring 540 includes a ring portion 543, a plurality of protrusion portions 541 spaced at a predetermined distance from each other and a plurality of extension portions 542.

Referring to FIG. 2B, FIG. 5 and FIG. 6B, the fastening ring 540 may be fastened to an outer peripheral surface of the support 100 to be rotated around the rotational shaft 310 of the driving part 300.

The fastening ring 540 may include the annular ring portion 543 having an inner lateral surface corresponding to the circumference of the frame 550, the plurality of protrusion portions 541 protruded to have a curved surface along a lower portion of the ring portion 543 and the extension portions 542 perpendicularly bent from the respective protrusion portions 541 toward a central axis of the fastening ring 540.

Referring to FIG. 6A, an inner lateral portion of each extension portion 542 facing a lower surface of the ring portion 543 may have a first inclined plane 542a slanted to one side along a rotational direction of the fastening ring 540. For example, as illustrated in FIG. 6A, the inner lateral portion of each extension portion 542 inside the fastening ring 540 may have the first inclined plane 542a of which an upper portion is slanted to one side when viewed from the front of the fastening ring 540.

Also, the support 100 illustrated in FIG. 2B and FIG. 6A may be formed into a circular plate shape including the first opening 110. Further, the support 100 may include the outer circular portion 170 including the plurality of circular arc-shaped insertion grooves 185 into which the respective extension portions 542 of the fastening ring 540 are inserted, and the inner circular groove 180 accommodating the extension portions 542 inserted through the insertion grooves 185.

For example, as illustrated in FIG. 6A, the extension portions 542 of the fastening ring 540 may be inserted into the insertion grooves 185 of the support 100. Here, the outer circular portion 170 may guide the protrusion portions 541 of the fastening ring 540 in order for the extension portions 542 to be accommodated in the inner circular groove 180.

The inner circular groove 180 may have a second inclined plane 180a slanted to one side so that an inner lateral portion facing an upper surface of the stereotactic surgical device 2 corresponds to the first inclined plane 542a of each extension portion 542. For example, as illustrated in FIG. 6A, the inner lateral portion of the inner circular groove 180 may have the second inclined plane 180a of which an upper portion is slanted to one side when viewed from the front of the support 100.

That is, after the extension portions 542 of the fastening ring 540 are inserted into the insertion grooves 180 of the support 100, the first inclined plane 542a of each extension portion 542 may be brought into contact with the second inclined plane 180a of the inner circular groove 180 by a rotational force of the fastening ring 540, and, thus, a compressive force between the connection part 500 and the support 100 may be generated.

Accordingly, even if the automated apparatus for stereotactic surgical device 1 of the present invention coupled to the handle 3 of the stereotactic surgical device 2 is slanted at a predetermined angle when a surgery is performed, it is possible to prevent separation between the support 100 and the connection part 500.

Also, since the fastening ring 540 of the connection part 500 is screw-coupled to the support 100, a fastening force between the support 100 and the connection part 500 can be improved.

Therefore, according to the present invention, it is possible to maximize contact between the automated apparatus for stereotactic surgical device 1 and the handle 3 which may be generated during rotation of the automated apparatus for stereotactic surgical device. Thus, stereotactic surgery can be performed more accurately and stably for a long time.

Meanwhile, the automated apparatus for stereotactic surgical device 1 according to an embodiment of the present invention may include a controller 600.

Figure 7:
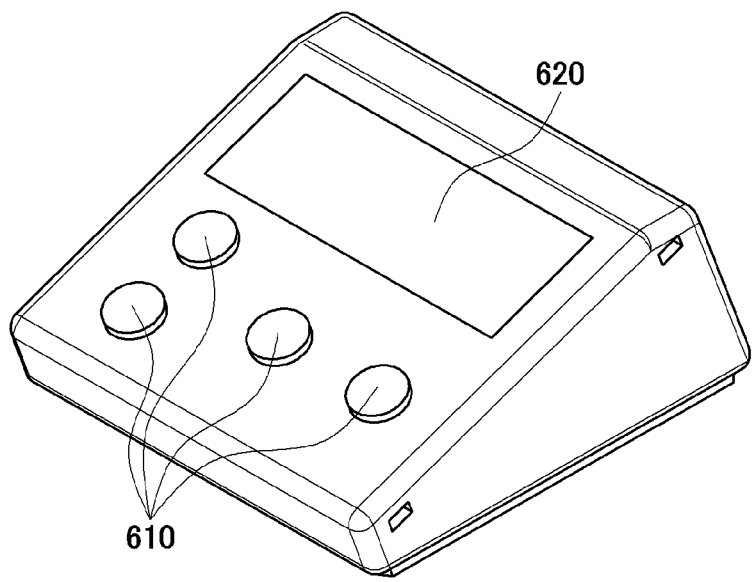
FIG. 7 illustrates a controller of the automated apparatus for stereotactic surgical device.

FIG. 7 illustrates a controller of the automated apparatus for stereotactic surgical device.

Referring to FIG. 7, the controller 600 may include an input member 610, a display member 620 and a control member.

The input member 610 may be composed of conventional buttons or a conventional touch panel installed on an outer surface of the controller 600, and the user may input an operational instruction by pressing or touching the input member 610 with a certain amount of force.

The display member 620 may function to output information related to an operation of the automated apparatus for stereotactic surgical device 1 of the present invention to the user. For example, the display member 620 may be configured as a conventional liquid crystal display or the like and may output information related to any one or more of an operation standby time of the rotational shaft 310, a time required for operation, a remaining operation time, a period of time from an operation standby time to an operation stop time, a moving speed of a surgical instrument of the stereotactic surgical device 2 and a moving range of the surgical instrument of the stereotactic surgical device 2.

The control member may calculate a time related to an operation of the rotational shaft 310, which will be output through the display member 620, and control the information output of the display member 620. The control member may control any one or more of a rotational direction, a rotational speed and an operation time of the rotational shaft 310, and may be configured as a conventional microcomputer or the like.

Further, the control member may calculate a rotational speed and an operation time of the rotational shaft 310 based on information about the required moving range and moving speed of the surgical instrument of the stereotactic surgical device 2 input by the user. Furthermore, the control member may control an operation of the rotational shaft 310 based on the calculated rotational speed and operation time of the rotational shaft 310.

Hereafter, an operation and effect of the automated apparatus for stereotactic surgical device according to the present invention will be described.

Figure 8:
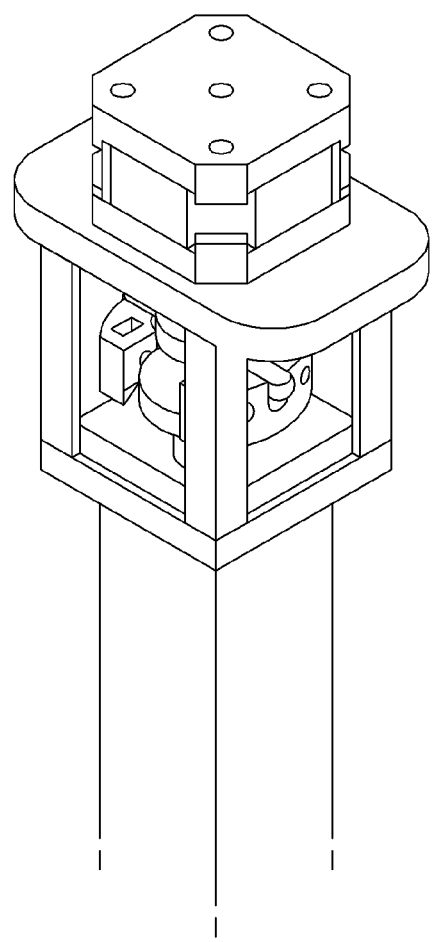
FIG. 8 illustrates the automated apparatus for stereotactic surgical device coupled to the stereotactic surgical device.

FIG. 8 illustrates the automated apparatus for stereotactic surgical device coupled to the stereotactic surgical device.

As illustrated in FIG. 8, the user may install the automated apparatus for stereotactic surgical device 1 in the stereotactic surgical device 2 to automatically operate the stereotactic surgical device 2.

Specifically, the user may couple the support 100 to a predetermined portion of the stereotactic surgical device 2 to allow the handle 3 of the stereotactic surgical device 2 to penetrate therethrough, and may couple the operation part 200 to the handle 3.

Specifically, the user may attach the connection part 500 coupled to the driving part 300 to the support 100 to automatically operate the stereotactic surgical device 2. When the connection part 500 is attached to the support 100, the insertion member 410 of the rotational part 400 is inserted into the first receiving groove 211 and the second receiving groove 221 of the operation part 200.

Then, the user may input a value for controlling rotation of the handle 3 through which the surgical instrument installed in the stereotactic surgical device 2 is manipulated by means of the input member 610 of the controller 600 and thus may operate the automated apparatus for stereotactic surgical device 1.

When the automated apparatus for stereotactic surgical device 1 is operated, the display member 620 of the controller 600 may output information about a time required for operation of the rotational shaft 310, a remaining operation time of the rotational shaft 310, and a moving speed and moving range of the surgical instrument of the stereotactic surgical device 2.

Meanwhile, the user may separate the connection part 500 from the support 100 to manually operate the automated stereotactic surgical device 2.

When the user separates the connection part 500 from the support 100 and the operation part 200 from the handle 3, the user may operate the stereotactic surgical device 2 by manually rotating the handle 3.

As described above, in the automated apparatus for stereotactic surgical device according to the present invention, the connection part coupled to the driving part is attached to the support coupled to the stereotactic surgical device so that the rotational part is coupled to the operation part coupled to the handle and rotates the operation part. Thus, the automated apparatus for stereotactic surgical device can automate the stereotactic surgical device.

Also, when the connection part coupled to the driving part is attached to the support, the rotational part is coupled to the operation part to switch the stereotactic surgical device into the automated stereotactic surgical device. When the connection part coupled to the driving part is detached from the support, the rotational part is separated from the operation part to switch the automated stereotactic surgical device into the stereotactic surgical device.

Further, the automated apparatus for stereotactic surgical device includes the controller capable of controlling an operation of the rotational shaft 310 of the driving part when the user inputs an instruction. Thus, the stereotactic surgical device can be controlled according to the user's instruction.

The above description of the present invention is provided for the purpose of illustration, and it would be understood by a person with ordinary skill in the art that various changes and modifications may be made without changing technical conception and essential features of the present invention. Thus, it is clear that the above-described examples are illustrative in all aspects and do not limit the present invention. For example, each component described to be of a single type can be implemented in a distributed manner. Likewise, components described to be distributed can be implemented in a combined manner.

The scope of the present invention is defined by the following claims rather than by the detailed description of the embodiment. It shall be understood that all modifications and embodiments conceived from the meaning and scope of the claims and their equivalents are included in the scope of the present invention.

We claim:

1. An automated apparatus for a stereotactic surgical device capable of applying a rotational force to a handle of the stereotactic surgical device, the automated apparatus comprising:
- a support that is formed into a plate shape including therein a first opening and is coupled to the stereotactic surgical device in order for the handle to penetrate therethrough the first opening;
- an operation part that is coupled to the handle penetrating the support and has a receiving groove, which is extended in a longitudinal direction, at an upper portion;
- a driving part that includes a rotational shaft;
- a rotational part that includes an insertion member extended in the longitudinal direction to be inserted into the receiving groove and is coupled to the rotational shaft, the rotational part being configured to rotate by the rotational shaft; and
- a connection part which is coupled to the driving part and receives the rotational part in a chamber formed therein and includes a second opening at a lower portion to communicate with the chamber and allow the operation part to be introduced thereinto and of which the lower portion is detachably coupled to the support,
- wherein when the connection part is attached to the support, the operation part is introduced into the second opening and the insertion member of the rotational part is inserted into the operation part, and when the connection part is detached from the support, the insertion member of the rotational part is separated from the operation part.

2. The automated apparatus for stereotactic surgical device of claim 1,
- wherein the operation part includes:
- a first operation member that includes a first receiving groove at an upper portion and a first contact surface, which is capable of being in contact with the handle, at a first lateral portion;
- a second operation member that includes a second receiving groove at an upper portion and a second contact surface, which faces the first contact surface and is capable of being in contact with the handle, at a second lateral portion; and
- a coupling member that couples the first operation member and the second operation member and is capable of adjusting a distance between the first operation member and the second operation member.

3. The automated apparatus for stereotactic surgical device of claim 2,
- wherein one end of the insertion member of the rotational part is inserted into the first receiving groove of the first operation member and another end thereof is inserted into the second receiving groove of the second operation member, and
- a transversal cross section of the insertion member has a wedge shape that tapers downwards, and
- the first receiving groove and the second receiving groove have a shape corresponding to the lower wedge shape of the insertion member and include a pair of slanted surfaces in contact with the wedge shape.

4. The automated apparatus for stereotactic surgical device of claim 2,
- wherein the coupling member includes:
- operation part bolts screw-coupled to the first operation member and the second operation member, respectively; and
- an operation part nut capable of fixedly coupling to a screw column.

5. The automated apparatus for stereotactic surgical device of claim 1,
- wherein the support includes:
- at least one support bolt;
- at least one support nut capable of being screw-coupled to the at least one support bolt;
- a plurality of bolt insertion holes, which is formed to allow the at least one support bolt to be inserted thereinto and faces each other, at a lateral portion of the support; and
- a nut insertion hole that is formed to communicate with the bolt insertion hole and penetrates an upper portion and a lower portion of the support to allow the support nut to be inserted thereinto, and
- when the support bolt inserted into the bolt insertion hole, which is screw-coupled to the support nut inserted into the nut insertion hole, is tightened, the support coupled to the stereotactic surgical device is fixed to the stereotactic surgical device.

6. The automated apparatus for stereotactic surgical device of claim 5,
- wherein the support includes a plurality of protrusions at the upper portion,
- the connection part includes a plurality of grooves at the lower portion, and
- the protrusions are freely inserted into the grooves or freely separated from the grooves, and
- when the protrusions are inserted into the grooves, lateral rotation and lateral movement between the connection part and the support are limited.

7. The automated apparatus for stereotactic surgical device of claim 1,
- wherein the connection part further includes:
- an annular fastening ring disposed under the chamber along the circumference of a frame including the second opening, and
- the fastening ring is fastened to an outer peripheral surface of the support to be rotated around the rotational shaft.

8. The automated apparatus for stereotactic surgical device of claim 7,
- wherein the fastening ring includes:
- an annular ring portion having an inner lateral surface corresponding to the circumference of the frame;
- a plurality of protrusion portions protruded to have a curved surface along a lower portion of the ring portion; and
- extension portions perpendicularly bent from the respective protrusion portions toward a central axis of the fastening ring, and
- an inner lateral portion of each extension portion facing a lower surface of the frame has a first inclined plane slanted to one side along a rotational direction of the fastening ring.

9. The automated apparatus for stereotactic surgical device of claim 8,
- wherein the plate shape includes: a circular plate shape, and
- wherein the support includes:
- an outer circular portion formed into the circular plate shape including the first opening and including a plurality of circular arc-shaped insertion grooves through which the extension portions of the fastening ring are inserted; and an inner circular groove accommodating the extension portions inserted through the insertion grooves, and the outer circular portion guides the protrusion portions of the fastening ring in order for the extension portions to be accommodated in the inner circular groove, and the inner circular groove has a second inclined plane slanted to one side so that an inner lateral portion facing the stereotactic surgical device corresponds to the first inclined plane of each extension portion, and when the first inclined plane of each extension portion is brought into contact with the second inclined plane of the inner circular groove by a rotational force of the fastening ring, a compressive force is applied.

10. The automated apparatus for stereotactic surgical device of claim 1,
wherein the rotational shaft is configured to be rotated by a step motor.

11. The automated apparatus for stereotactic surgical device of claim 1, further comprising:

a controller capable of controlling any one or more of a rotational direction, a rotational speed and an operation time of the rotational shaft.

12. The automated apparatus for stereotactic surgical device of claim 11,
wherein the controller includes:
an input member that receives a user's operational instruction; and
a display member that displays any one or more of a time required for operating the rotational shaft, a remaining operation time of the rotational shaft, a moving speed of a surgical instrument of the stereotactic surgical device and a moving range of the surgical instrument, and
the rotational speed and the operation time of the rotational shaft are calculated based on the required moving range and moving speed of the surgical instrument input by the user.

* * * * *